US009655771B1

(12) United States Patent
Sauls

(10) Patent No.: US 9,655,771 B1
(45) Date of Patent: May 23, 2017

(54) STRETCHABLE HEATED WRAP SYSTEM

(71) Applicant: Kate S. Sauls, Pinellas Park, FL (US)

(72) Inventor: Kate S. Sauls, Pinellas Park, FL (US)

( * ) Notice: Subject to any disclaimer, the term of this patent is extended or adjusted under 35 U.S.C. 154(b) by 342 days.

(21) Appl. No.: 14/308,211

(22) Filed: Jun. 18, 2014

(51) Int. Cl.
*A61F 13/00* (2006.01)
*A61F 7/02* (2006.01)
*A61H 1/00* (2006.01)
*A61F 7/00* (2006.01)

(52) U.S. Cl.
CPC ............... *A61F 7/02* (2013.01); *A61F 7/007* (2013.01); *A61F 7/0241* (2013.01); *A61H 1/008* (2013.01); *A61F 2007/0231* (2013.01); *A61F 2007/0268* (2013.01)

(58) Field of Classification Search
CPC ........ A61H 2201/00; A61H 2201/0134; A61H 2201/0157; A61H 2201/02; A61H 2201/0207; A61H 2201/0221; A61H 2201/0228; A61H 2201/0242; A61H 2201/0257; A61H 2201/0292; A61H 2201/1654; A61H 2201/1683; A61H 2201/1685; A61H 2201/1688; A61H 1/008; A61F 7/02; A61F 7/007; A61F 7/0241; A61F 2007/0231; A61F 2007/0268
See application file for complete search history.

(56) References Cited

U.S. PATENT DOCUMENTS

| | | | | |
|---|---|---|---|---|
| 3,900,035 A * | 8/1975 | Welch | ........................ | A61F 7/10 607/108 |
| 4,676,247 A * | 6/1987 | Van Cleve | ................ | A61F 7/02 607/112 |
| 5,005,374 A * | 4/1991 | Spitler | ............... | A41D 13/0055 2/171.2 |
| 5,065,758 A * | 11/1991 | Whitehead | ................ | A61F 7/10 604/113 |
| 5,086,629 A * | 2/1992 | Dibrell | ................. | A41D 13/005 401/6 |
| 5,304,216 A * | 4/1994 | Wallace | ................ | A61F 7/0241 607/108 |
| 5,427,563 A * | 6/1995 | Manning | ................... | A61F 7/02 2/73 |
| 5,628,772 A * | 5/1997 | Russell | ...................... | A61F 7/10 601/112 |
| 5,848,981 A * | 12/1998 | Herbranson | .............. | A61F 7/10 601/134 |
| 6,050,265 A * | 4/2000 | Richardson | ............ | A61G 7/065 128/845 |
| 6,231,596 B1 * | 5/2001 | Collins | ..................... | A61F 7/00 126/263.02 |

(Continued)

*Primary Examiner* — Steven Douglas

(57) ABSTRACT

A wrapper has an inner edge and an outer edge separated by a length. The wrapper has a first side edge and a second side edge separated by a width. The wrapper has an interior sheet and an exterior sheet. The interior sheet and the exterior sheet are fabricated from yarn with stretchable and elastic characteristics. Hook and loop fasteners couple the interior sheet adjacent to the outer edge to the exterior sheet. A plurality of pockets are formed between the interior sheet and the exterior sheet by rows of stitching between the first side edge and the second side edge. A quantity of temperature retentive material is within the pockets. Optional components include an electrical wire to facilitate heating and a container to facilitate heating and/or cooling.

6 Claims, 5 Drawing Sheets

(56) References Cited

U.S. PATENT DOCUMENTS

| | | | | |
|---|---|---|---|---|
| 6,256,818 B1 * | 7/2001 | Hughes | ............... | A47G 9/1036 |
| | | | | 5/421 |
| 6,554,787 B1 * | 4/2003 | Griffin | ...................... | A61F 7/02 |
| | | | | 601/70 |
| 6,656,210 B1 * | 12/2003 | Plewes | ...................... | A61F 7/02 |
| | | | | 128/DIG. 15 |
| 8,209,995 B2 * | 7/2012 | Kieling | ................. | A45C 3/001 |
| | | | | 220/907 |
| D713,534 S * | 9/2014 | Manley, Jr. | .................. | D24/189 |
| 2002/0068886 A1 * | 6/2002 | Lin | ...................... | A61H 9/0078 |
| | | | | 601/15 |
| 2004/0260211 A1 * | 12/2004 | Maalouf | ............... | A61H 23/02 |
| | | | | 601/15 |
| 2006/0241534 A1 * | 10/2006 | Tsai | ...................... | A61H 7/001 |
| | | | | 601/15 |
| 2008/0033326 A1 * | 2/2008 | Evans | .................... | A61H 23/02 |
| | | | | 601/15 |
| 2014/0358202 A1 * | 12/2014 | Zanella | ................. | A61H 23/02 |
| | | | | 607/108 |

* cited by examiner

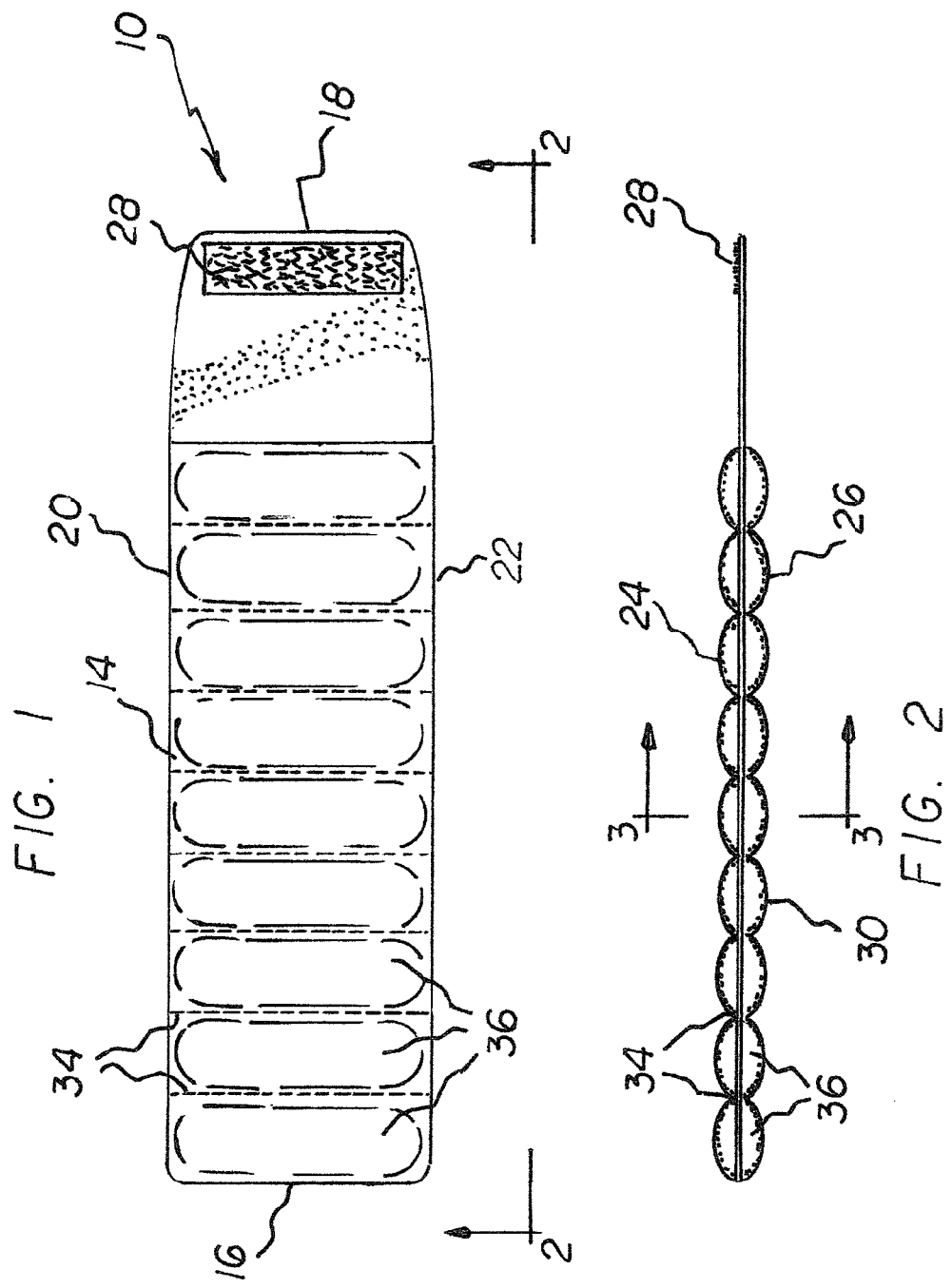

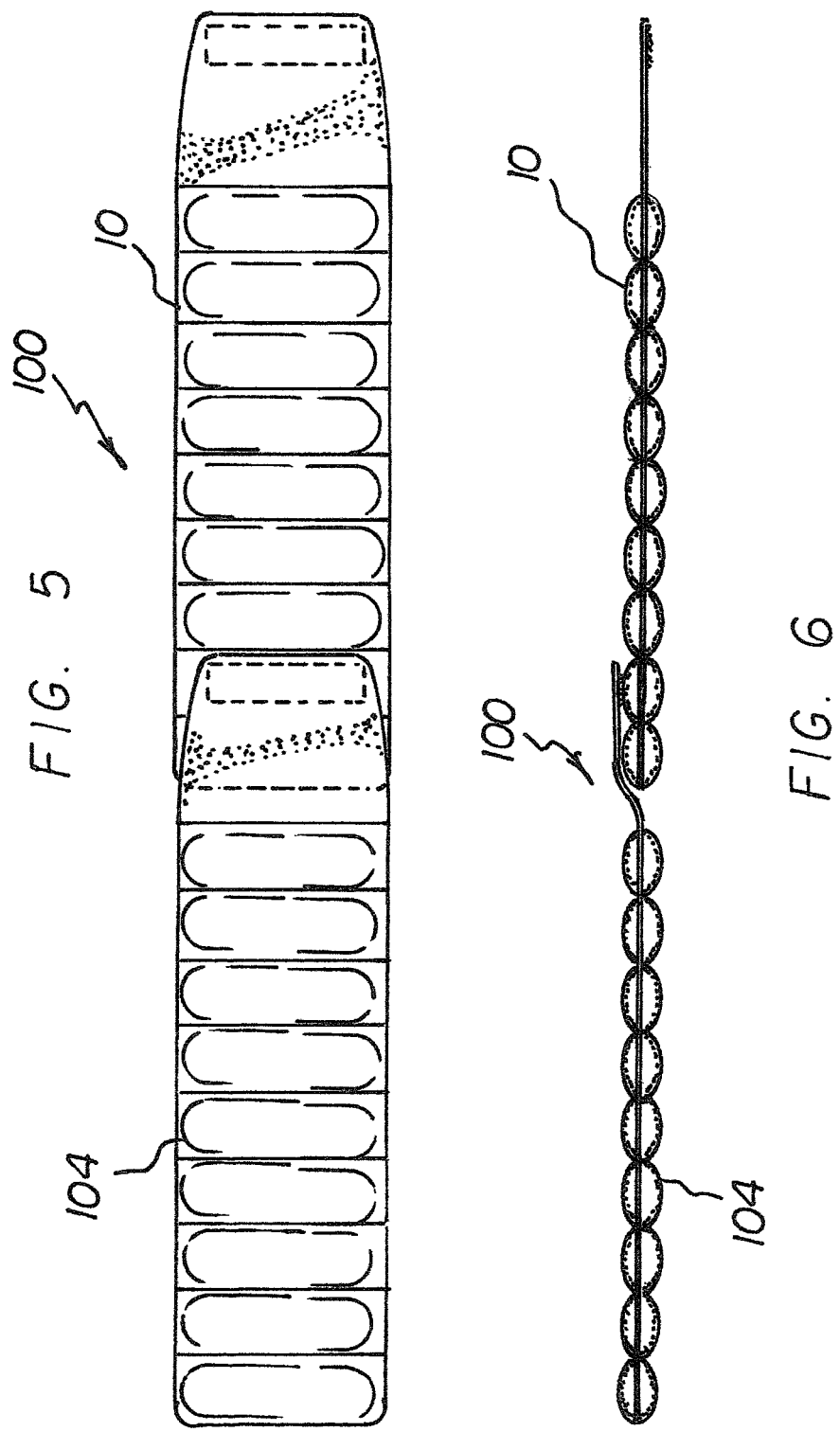

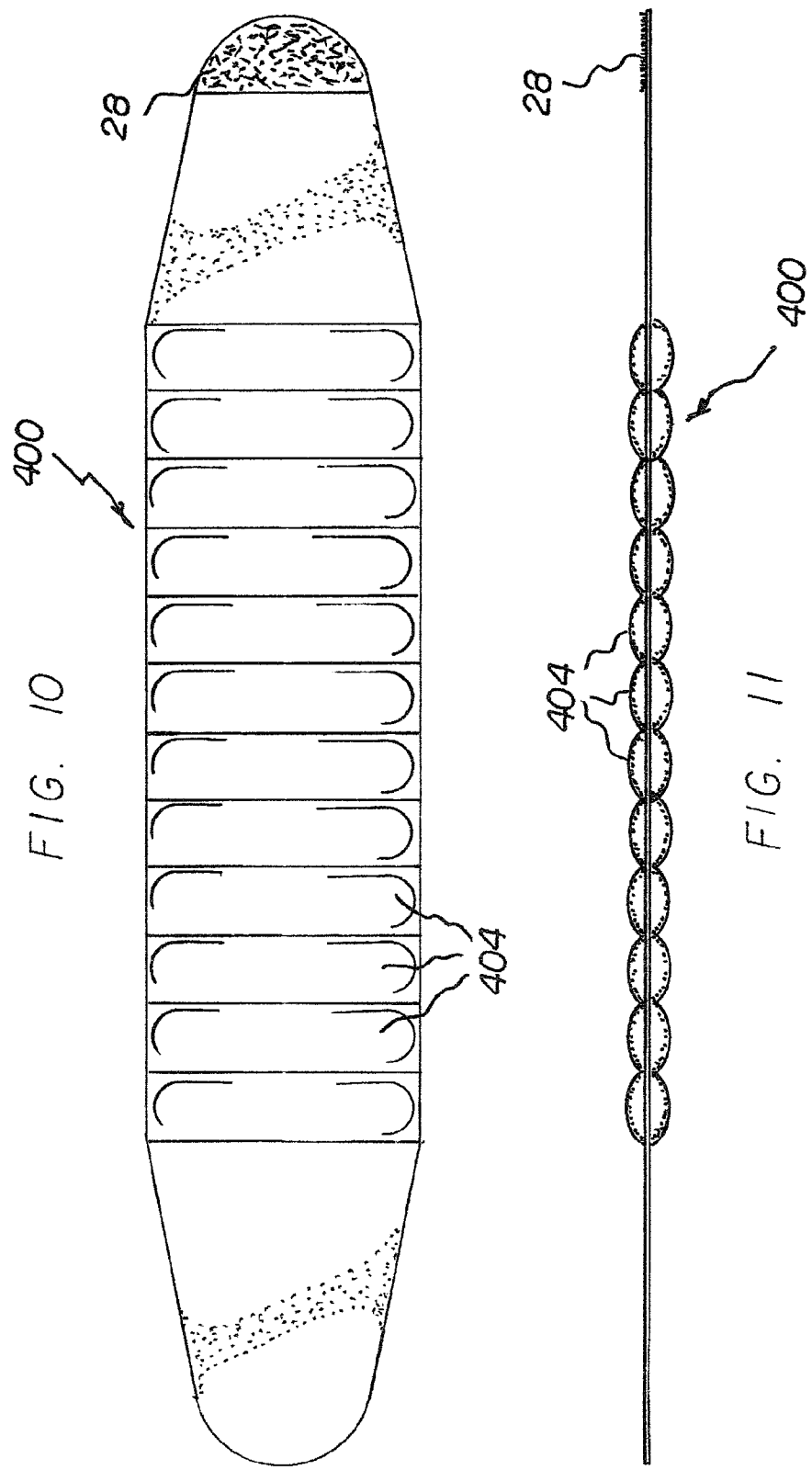

STRETCHABLE HEATED WRAP SYSTEM

BACKGROUND OF THE INVENTION

Field of the Invention

The present invention relates to a stretchable heated wrap system and more particularly pertains to wrapping infirm body parts of users and heating the wrapped body parts while exerting compressive forces for beneficial purposes, the wrapping, heating, exerting, and benefiting being done in a safe, convenient, and economical manner.

SUMMARY OF THE INVENTION

In view of the foregoing disadvantages inherent in the known types of wrap systems of known designs and configurations now present in the prior art, the present invention provides an improved stretchable heated wrap system. As such, the general purpose of the present invention, which will be described subsequently in greater detail, is to provide a stretchable heated wrap system and method which has all the advantages of the prior art and none of the disadvantages.

To attain this, the present invention essentially comprises a wrapper. The wrapper has an inner edge. The wrapper has an outer edge. The inner edge and the outer edge are separated by a length. The wrapper has a first side edge. The wrapper has a second side edge. The first side edge and the second side edge are separated by a width. The wrapper has an interior sheet. The wrapper has an exterior sheet. The interior sheet and the exterior sheet include threads with stretchable and elastic characteristics. Hook and loop fasteners are provided. The hook and loop fasteners couple the interior sheet adjacent to the outer edge to the exterior sheet. A plurality of pockets is also provided. The pockets are provided between the interior sheet and the exterior sheet. The pockets are formed by rows of stitching. The rows of stitching extend between the first side edge and the second side edge. Provided last is a quantity of temperature retentive material. The temperature retentive material is provided within the pockets.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a stretchable heated wrap system which has all of the advantages of the prior art wrap systems of known designs and configurations and none of the disadvantages.

It is another object of the present invention to provide a stretchable heated wrap system which may be easily and efficiently manufactured and marketed.

It is further object of the present invention to provide a stretchable heated wrap system which is of durable and reliable constructions.

An even further object of the present invention is to provide a stretchable heated wrap system which is susceptible of a low cost of manufacture with regard to both materials and labor, and which accordingly is then susceptible of low prices of sale to the consuming public, thereby making such stretchable heated wrap system economically available to the buying public.

Lastly, another object of the present invention is to provide a stretchable heated wrap system for wrapping infirm body parts of users and heating the wrapped body parts while exerting compressive forces for beneficial purposes, the wrapping, heating, exerting, and benefiting being done in a safe, convenient, and economical manner.

These together with other objects of the invention, along with the various features of novelty which characterize the invention, are pointed out with particularity in the claims annexed to and forming a part of this disclosure.

For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a front elevational view of a stretchable heated wrap system constructed in accordance with the principles of the present invention.

FIG. 2 is a side elevational view taken along line 2-2 of FIG. 1.

FIG. 5 is a front elevational views similar to FIG. 1 but with two wraps coupled together for encircling a larger body part.

FIG. 6 is a side elevational view taken along line 6-6 of FIG. 5.

FIG. 10 is a front elevational views similar to FIGS. 1 and 5 but with a wrap of a larger size for encircling a larger body part such as a torso.

FIG. 11 is a side elevational view taken along line 11-11 of FIG. 10.

The same reference numerals refer to the same parts throughout the various Figures.

DESCRIPTION OF THE PREFERRED EMBODIMENT

Figure 3:
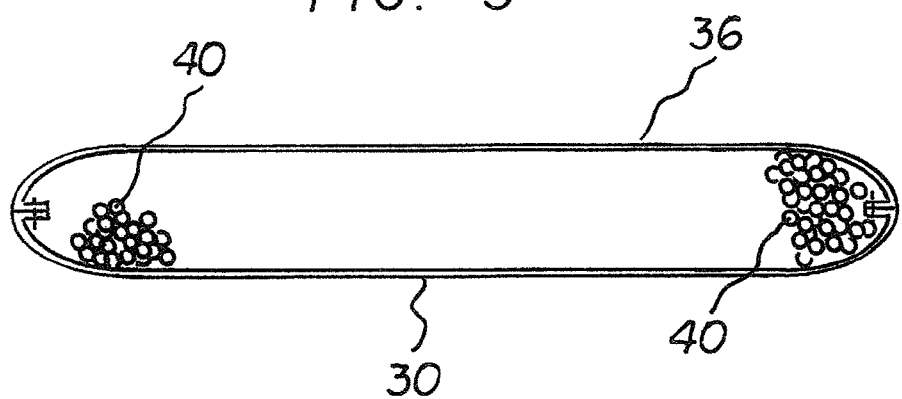
FIG. 3 is a cross sectional view taken along line 3-3 of FIG. 2.
Figure 4:
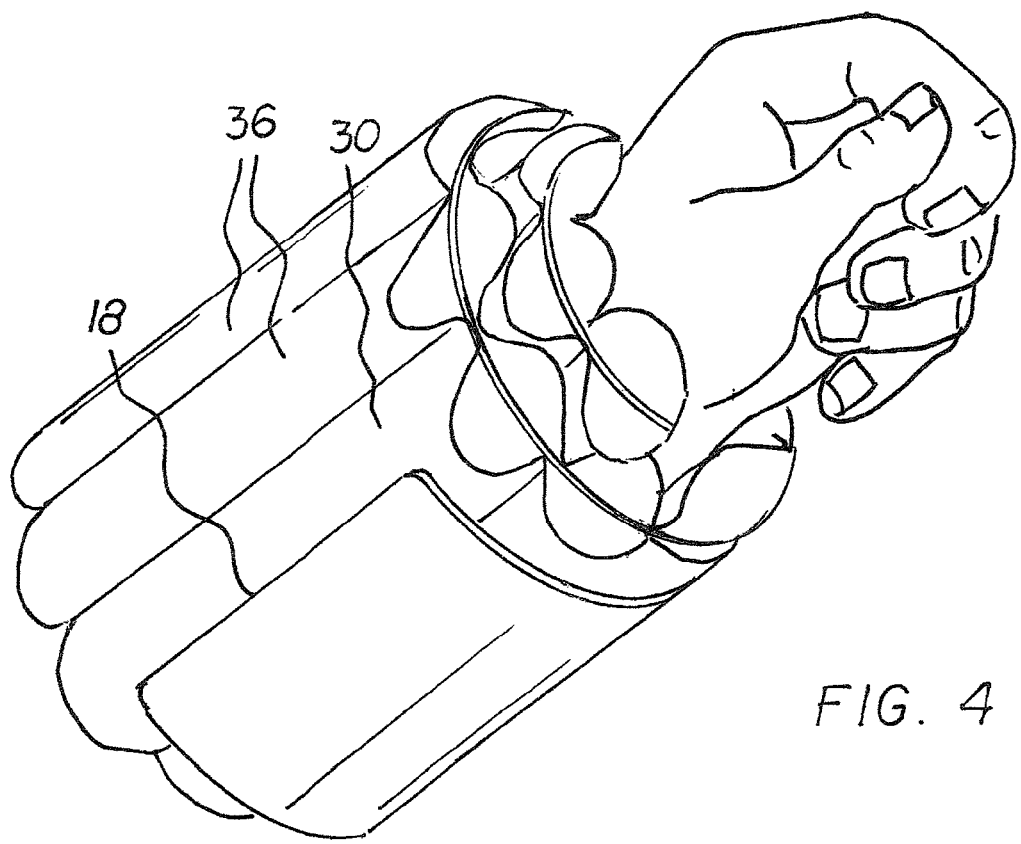
FIG. 4 is a perspective illustration of the wrap in use, wrapped around the wrist of a user, a smaller body part.

With reference now to the drawings, and in particular to FIG. 1 thereof, the preferred embodiment of the stretchable and elastic heated wrap system embodying the principles and concepts of the present invention and generally designated by the reference numeral 10 will be described.

The present invention, the stretchable heated wrap system 10 is comprised of a plurality of components. Such components in their broadest context include a wrapper, pockets, temperature retentive material. Such components are individually configured and correlated with respect to each other so as to attain the desired objective.

First provided is a wrapper 14. The wrapper is in generally rectangular configuration. The wrapper has an inner edge 16. The wrapper also has a parallel outer edge 18. The inner edge and the outer edge are separated by a length of from 15 inches to 18 inches. The wrapper has a first side edge 20. The wrapper also has a parallel second side edge 22. The first side edge and the second side edge are separated by a width of from 7 inches to 8 inches. The wrapper has an interior sheet 24. The wrapper also has an exterior sheet 26. The interior sheet and the exterior sheet are separated by a varying thickness. The thickness has a maximum thickness of 1 inch, plus or minus 10 percent. The interior sheet is knit from yarn which includes threads with stretchable and elastic characteristics. The interior sheet has a smooth exposed exterior surface. The exterior sheet is knit from yarn which includes threads with stretchable and elastic characteristics. The exterior sheet has an exposed exterior surface. The exposed exterior surface has loops 28 of a hook and loop fasteners. The interior sheet adjacent to the outer edge has a patch of hooks 30 of the hook and loop fasteners. The patch of hooks extends from the outer edge from 5 percent to 10 percent of the length of the wrapper.

Further provided are nine rows of stitching 34. The rows of stitching are provided between the first side edge and the second side edge. In this manner nine pockets 36 are formed. The nine rows of stitching are provided parallel with the inner edge and outer edge. The nine rows of stitching begin at the inner edge. The nine rows of stitching are spaced by 1.5 inches plus or minus 20 percent. The interior sheet and the exterior sheet are provided in facing contact at regions remote from the pocket.

In the preferred embodiment, the wrapper has from 8 to 10 pockets with a length of from 15 inches to 18 inches and a width of from 7 inches and 8 inches. Note FIGS. 1-4.

Provided last is a quantity of heat retentive material 40. The heat retentive material is provided within the pockets. The heat retentive material is chosen from the class consisting of long grained white rice, flax seed, buckwheat, barley, oatmeal, feed corn, cherry pits, beans, millet seed, thermal gel beads, clays, and other phase changing materials. The white rice is not instant rice which might undesirably cook.

The heat retentive material is adapted to be heated in a conventional or microwave oven. The heat retentive material is adapted to slowly dissipate such heat over time during use when wrapped around a body part of a user. The wrapper with the pockets and the quantity of heat retentive material is adapted to stretch. The heat retentive material is adapted to stretch from an unstretched length to an extended stretched length. The unstretched length is from 15 to 18 inches. The extended stretched length is 30 percent to 50 percent greater than the unstretched length. The wrapper with heated heat retentive material is adapted to be stretched around a body part of a user. The hooks are coupled to the loop. In this manner heat and compressive pressure are applied to a malady for beneficial purposes.

Temperature retentive material is intended to define material adapted to accept heat when subjected to elevated temperatures, as through a conventional or microwave oven, and then adapted to slowly dissipate such heat over time. It is also intended to define material adapted to accept cold when subjected to reduced temperatures, as through a refrigerator or a freezer, and then adapted to slowly dissipate such cold over time.

In this alternate embodiment 100 of the present invention, at least one supplemental wrapper 104 is provided. The supplemental wrapper is adapted to couple to the first recited wrapper 14. In this manner a large body part of a user is encompassed. Note FIGS. 5-6.

Figure 7:
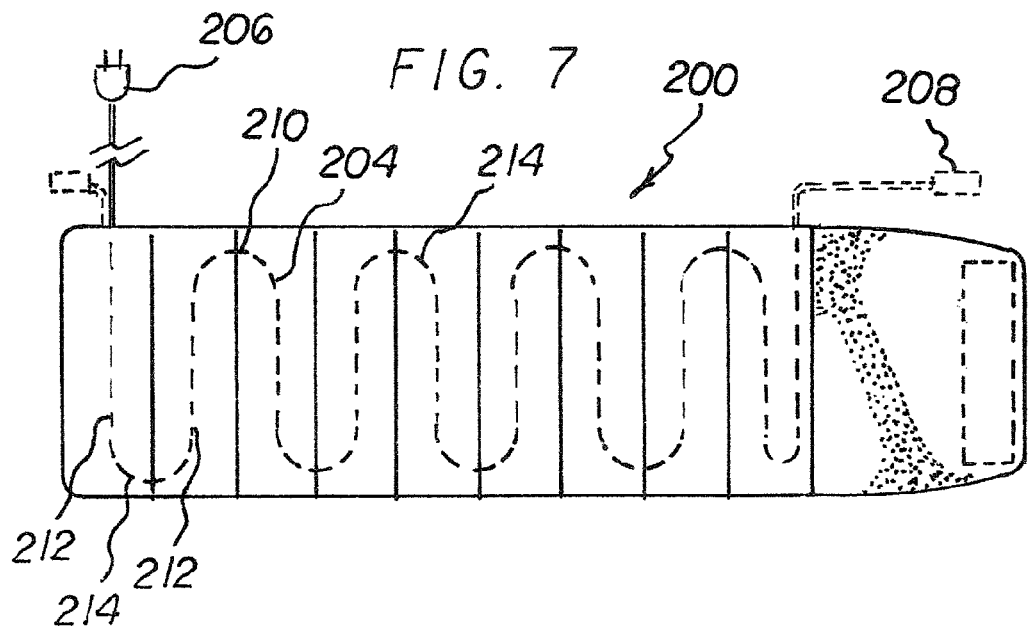
FIG. 7 is a front elevational view similar to FIG. 1 but illustrating an alternate embodiment of the invention, a wrap with an electrical heater.

In another alternate embodiment 200 of the present invention, an electrical heater wire 204 is provided. The electrical heater wire has an input end. The input end has a plug 206. The plug is adapted to be plugged into a source of electrical potential. The plug is provided remote from the wrapper adjacent to the inner edge. The electrical heater wire has an output end. The output end has a receptacle 208. The receptacle is adapted to receive a plug of a supplemental system. Not shown. The receptacle is provided remote from the wrapper adjacent to the outer edge. The electrical heater wire has a central extent 210. The central extent is in a serpentine configuration. The central extent has linear sections 212. The linear sections are provided within the pockets. The central extent also has arcuate sections 214. The arcuate sections couple the linear sections of adjacent pockets. Note FIG. 7.

Figure 8:
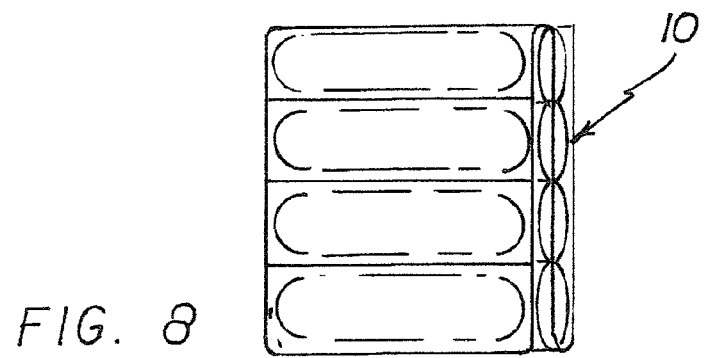
FIG. 8 is an exploded view of another alternate embodiment of the invention, a wrap with a container.
Figure 9:
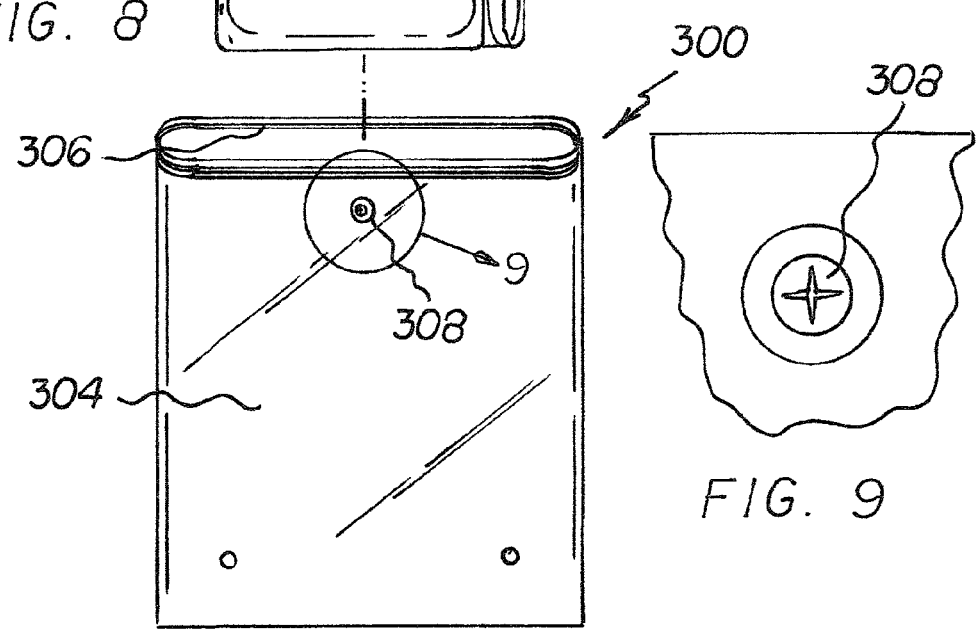
FIG. 9 is an enlarged illustration of the valve taken at circle 9 of FIG. 8.

In the next alternate embodiment 300 of the present invention, a container is provided. The container is a plastic bag 304. The plastic bag is of a size to removably receive the wrapper while being heated in a conventional or microwave oven prior to use. The plastic bag has an opening. The opening has a slide fastener 306. In this manner the plastic bag may be closed. The plastic bag has a two way valve 308 or hole. In this manner, the two way valve or hole allows extra pressure to be vented while keeping the moisture on the wrapper while being heated. Note FIGS. 8 and 9.

As an alternative to a plastic bag, a freezer-safe and/or microwave-safe box container with a lid may be utilized. In such box container, a two way valve or hole is preferably provided as in the bag. Such bag and box-container keep odors from transferring between contents of a freezer and the present invention.

In the last alternate embodiment 400 of the present invention, the wrapper has from 11 to 13 pockets 404. The pockets have a length. The length of the pockets is from 34 inches to 38 inches. The pocket have a width. The width is from 9 inches to 11 inches. Note FIGS. 10-11.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those

What is claimed as being new and desired to be protected by Letters Patent of the United States is as follows:

1. A stretchable heated wrap system comprising:
a primary wrapper having an inner edge and an outer edge separated by a length, the primary wrapper having a first side edge and a second side edge separated by a width, the primary wrapper having an interior sheet and an exterior sheet, the interior sheet and the exterior sheet being fabricated from yarn which is stretchable and elastic, hook and loop fasteners coupling the interior sheet adjacent to the outer edge to the exterior sheet;
a plurality of pockets between the interior sheet and the exterior sheet, the pockets being formed by rows of stitching extending between the first side edge and the second side edge;
a quantity of temperature retentive material within the pockets; and
an electrical heater wire (204), the electrical heater wire having an input end with a plug (206) adapted to be plugged into a source of electrical potential, the plug being remote from the wrapper adjacent to the inner edge, the electrical heater wire having an output end with a receptacle (208) adapted to receive a plug of a supplemental system, the receptacle being remote from the primary wrapper adjacent to the outer edge, the electrical heater wire having a central extent (210) in a serpentine configuration with linear sections (212) within the pockets and with arcuate sections (214) coupling the linear sections of adjacent pockets.

2. The system as set forth in claim 1 wherein the primary wrapper has from 8 to 10 pockets with a length of from 15 inches to 18 inches and a width of from 7 inches and 8 inches.

3. The system (100) as set forth in claim 1 and further including:
at least one supplemental wrapper (104) adapted to couple to the primary wrapper (14) for encompassing a large body part of a user.

4. A stretchable heated wrap system comprising:
a wrapper having an inner edge and an outer edge separated by a length, the wrapper having a first side edge and a second side edge separated by a width, the wrapper having an interior sheet and an exterior sheet, the interior sheet and the exterior sheet being fabricated from yarn which is stretchable and elastic, hook and loop fasteners coupling the interior sheet adjacent to the outer edge to the exterior sheet;
a plurality of pockets between the interior sheet and the exterior sheet, the pockets being formed by rows of stitching extending between the first side edge and the second side edge;
a quantity of temperature retentive material within the pockets; and
a container (304) being of a size to removably receive the wrapper while being heated in an oven prior to use, the container having a closure (306), the container having a two way valve (308) allowing extra pressure to be vented while being heated.

5. The system (400) as set forth in claim 1 wherein the wrapper has from 11 to 13 pockets (404) with a length of from 34 inches to 38 inches and a width of from 9 inches to 11 inches.

6. A stretchable heated wrap system (10) for wrapping infirm body parts of users and heating the wrapped body parts while exerting compressive forces for beneficial purposes, the wrapping, heating, exerting, and benefiting being done in a safe, convenient, and economical manner, the system comprising, in combination:
a wrapper (14) having a generally rectangular configuration, the wrapper having an inner edge (16) and a parallel outer edge (18) separated by a length of from 15 inches to 18 inches, the wrapper having a first side edge (20) and a parallel second side edge (22) separated by a width of from 7 inches to 8 inches, the wrapper having an interior sheet (24) and an exterior sheet (26) separated by a maximum thickness of 1.1 inches, the interior sheet being knit from yarn which is stretchable and elastic with a smooth exposed exterior surface, the exterior sheet being knit from yarn which is stretchable and elastic, with an exposed exterior surface formed with loops (28) of a hook and loop fastener, the interior sheet adjacent to the outer edge having a patch of hooks (30) of the hook and loop fasteners, the patch of hooks extending from the outer edge, the patch of hooks having a patch length, the wrapper having a wrapper length from 5 percent to 10 percent of the wrapper length;
nine rows of stitching (34) extending between the first side edge and the second side edge forming nine pockets (36), the nine rows of stitching being parallel with the inner edge and outer edge, the nine rows of stitching beginning at the inner edge, the nine rows of stitching being spaced by 1.5 inches, the interior sheet and the exterior sheet being in facing contact at regions remote from the pocket; and
a quantity of heat retentive material (40) within the pockets, the heat retentive material being chosen from the class of heat retentive material consisting of long grained white rice, flax seed, buckwheat, barley, oatmeal, feed corn, cherry pits, beans, millet seed, and thermal gel beads, the heat retentive material adapted to be heated in an oven and slowly dissipate such heat over time during use when wrapped around a body part of a user, the wrapper with the pockets and the quantity of heat retentive material adapted to stretch from an unstretched length of from 15 to 18 inches to an extended stretched length of 30 percent to 50 percent greater than the unstretched length, the wrapper with heated heat retentive material adapted to be stretched around a body part of a user with the hooks coupled to the loops to provide heat and compressive pressure for beneficial purposes.

* * * * *